US00PP08453P

United States Patent [19]

Moore

[11] Patent Number: Plant 8,453

[45] Date of Patent: Nov. 9, 1993

[54] MINIATURE ROSE PLANT NAMED 'POLY'

[75] Inventor: Ralph S. Moore, Visalia, Calif.

[73] Assignee: Sequoia Nursery, Visalia, Calif.

[21] Appl. No.: 989,526

[22] Filed: Dec. 11, 1992

[51] Int. Cl.[5] ..... A01H 5/00

[52] U.S. Cl. ..... Plt./8.2

[58] Field of Search ..... Plt./8.2

*Primary Examiner*—Howard J. Locker

*Assistant Examiner*—Elizabeth C. Kemmerer

[57] ABSTRACT

The subject of the present disclosure is a new and distinct cultivar of miniature rose plant characterized primarily by medium yellow buds and flowers and further identified by the well foliaged plant.

1 Drawing Sheet

The present invention relates to a new and distinct cultivar of hardy, dwarf, bush type rose plant of the miniature class; the cultivar being primarily characterized—as to novelty— by medium yellow buds and flowers, the general color effect being yellow.

The cultivar is further characterized by:

An abundance of bloom, with flowers borne singly or several to the stem in loose clusters.

Little or no fragrance.

A plant which is vigorous, of somewhat upright habit with semi-glossy, medium size foliage with pointed leaflets; the buds and flowers being similar in form to Rise'N Shine (miniature — U.S. Plant Pat. No. 4,231) but slightly larger in size.

The plant, which has a normal height of 16–18 inches or more, can easily be maintained at lesser height by occasional trimming.

A plant which grows and blooms satisfactorily both in greenhouse and outdoors; is good for growing in pots; and provides excellent garden decoration as well as cut flowers.

The present cultivar of miniature rose was originated by me at my nursery located at Visalia, Calif., under conditions of careful control and observation, as a cross between an un-named miniature seedling — (Little Darling X Yellow Magic) as the seed parent and Gold Badge (Floribunda—U.S. Plant Pat. No. 4,625), as the pollen parent.

Subsequent to origination of the variety I successfully asexually reproduced it at the same nursery, located as aforesaid, by budding as well as by cuttings; the reproductions having run true in all respects.

The color photograph illustrates the cultivar, including the foliage, buds and flowers.

Referring now specifically to the new and distinct cultivar of miniature rose plant, the following is a detailed description thereof in outline; all major color plate identifications being by reference to The Royal Horticultural Society Colour Chart, except where common terms of color definition are employed.

Type: Hardy; dwarf; bushy; upright; seedling, greenhouse; outdoors; cut flowers; garden decoration; potted plant.

Class: Miniature. Cultivar identification: Morpoly (Commercial synonym: Cal Poly).

Flowers borne: several together in loose clusters or sprays, but sometimes singly on slender, wirey stems.

Quantity of bloom: abundant both outside and in greenhouse.

Bud:

*Peduncle.*—Medium length; slender but sturdy; erect; medium green; hairs — numerous very short fuzz-like hairs. Before calyx breaks; size — small.

*Form.*—Long; pointed, essentially smooth, and occasional foliaceous appendages on surface of bud; with foliaceous parts extending beyond the tip of the bud equal to one-half or more of its length.

*Color.*—Medium green. As calyx breaks, color — yellow to greenish yellow.

*Opening.*—Opens well in all weather.

Bloom:

*Size when fully open.* —Small, averaging about 40 mm (1¾")

*Petalage.*—Double — averaging about 24–28 petals, arranged regularly plus occasional petaloids.

*Form.*—High centered to cupped at first, becoming more open, with petals rolled loosely outward, and later at maturity open with petals remaining in similar shape and position. Petals tend to fold back at edges, giving each petal a pointed effect. Open flowers show stamens.

*Sepals.*—Permanent, spear shaped, recurved.

Petals: Fairly thick; satiny on inside and on outside surface;

*Shape.*—Outside petals, broad lanceolate (rounded) with very short acute tip; intermediate — broad lanceolate, with very small acute tip; inside — lanceolate with acute or rounded tip.

*Color.*—Newly opened flower from a plant grown outdoors October, 1992, Visalia, Calif. Outside petal: Outside surface — yellow, near Yellow Group 12A. Inside surface — yellow, near Yellow Group 12A (similar to outside surface). Note: The yellow color of this cultivar is generally longer lasting and more stable than other yellow cultivars and is thus less inclined to fade. Intermediate petal. Outside surface — similar to outside petal. Inside surface — similar to outside petal. Inner petal: Outside surface — similar to intermediate petal; inside surface — similar to intermediate petal. General color effect; newly opened flowers — color bright yellow. Three days open — color similar to fresh open flower. Behavior — opens well in all weather. Spent petals hang on. Flower longevity (Aug. 1992) — plant in pot 6–8 days or longer. Cut flowers at living room temperature 4–5 days.

Reproductive organs:

*Stamens.*—Abundant, arranged regularly about pistils.

*Filaments.*—Varying length, medium to long, yellow.

*Anthers.*—Well formed; yellow.

*Pollen.*—Abundant amount.

*Pistils.*—Average number.

*Styles.*—Fairly even; medium length; bunched; color — redish.

*Stigmas.*—Pinkish.

*Ovaries.*—All enclosed in calyx.

*Hips.*—Several — shape rounded; color — orange to russett.

*Seeds.*—Several.

Foliage:

*Leaves.*—Compound of five leaflets (sometimes 3 or 7). Size — medium small; leathery; semi-glossy.

*Leaflets.*—Shape: broad lanceolate; apex acute; base rounded. Margin serrate.

*Color.*—Medium green; new growth — medium green with margin tinted reddish or bronze.

*Rachis.*—Medium strength; upper side may have a few tiny short hairs or prickles, grooved; underside — several small hooked thorns.

*Stipules.*—Medium long; narrow to medium width; short length narrow points which turn out usually at about 45 degrees.

Growth:

*Habit.*—Dwarf; bushy; rounded much branched.

*Growth.*—Free vigorous; internodes short.

*Canes.*—Medium; slender; sturdy.

*Main stems.*—Color; medium green. Thorns: few; slender; straight; inclined slightly downward; color — brown. Prickles — none; hairs — none.

*Branches.*—Color: light to medium green. Thorns: few to none; medium length; slender; nearly straight, inclined slightly downward. Medium oval base. Prickles: few or none. Hairs: none.

*Young shoots.*—Color: light to medium green. Thorns: few to none, slender; straight, inclined slightly downward; color — greenish (or bronzy)

The miniature rose plant and its flowers as herein described may vary in slight detail due to climatic, soil and cultural conditions under the cultivar may be grown; the present description being of the cultivar as grown at Visalia, Calif.

The following is claimed:

1. A new and distinct cultivar of miniature rose plant of hardy, dwarf, bushy, rounded, upright, much branched habit substantially as illustrated and described, characterized by buds and flowers which are essentially yellow in color, the buds and flowers resembling Rise'N Shine in shape but slightly larger in size, and further characterized by a plant which is vigorous and compact, easy to propagate from soft wood cuttings or by budding, with an abundance of flowers borne singly or several to the stem in loose clusters.

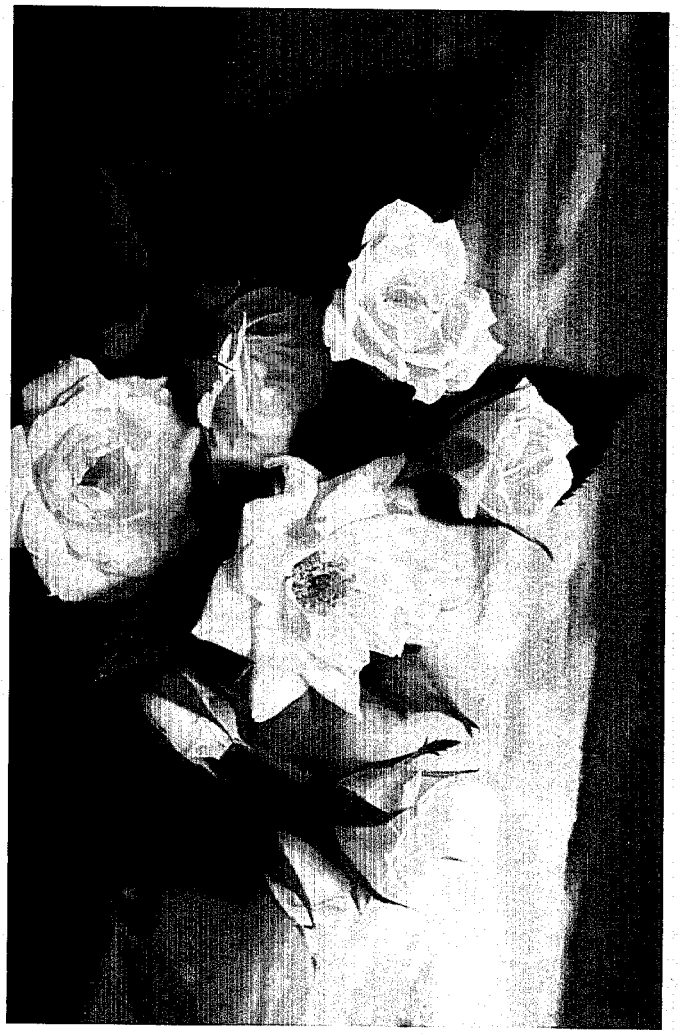

* * * * *